United States Patent [19]

Weeks

[11] Plant 4,006

[45] Jan. 4, 1977

[54] ROSE PLANT

[76] Inventor: O. L. Weeks, 926 W. Philadelphia, Ontario, Calif. 91761

[21] Appl. No.: 668,975

[22] Filed: Mar. 22, 1976

[51] Int. Cl.[2] ..... A01H 5/00
[52] U.S. Cl. ..... Plt./11
[58] Field of Search ..... Plt./11, 22

*Primary Examiner*—Robert E. Bagwill
*Attorney, Agent, or Firm*—Frank B. Robb

CLAIM

A new and distinct variety of rose plant of the hybrid tea class, substantially as herein shown and described, characterized particularly as to novelty by the unique combination of an extremely vigorous habit of growth which promotes repeat blooming cycles; constancy of bloom throughout the year; a carnation-like full flower form; and a distinctive and attractive flower color of many shadings, ranging from an almost pure pale yellow color, at times, to a definite "freckled" effect at other times.

1 Drawing Figure

The present invention relates to a new and distinct variety of rose plant of the hybrid tea class, which was originated by me by crossing an unnamed and unpatented rose seedling (identified in my breeding records as No. 6671-17) with the rose variety known as "Granada" (U.S. Plant Pat. No. 2,214), the former being the seed parent and the latter being the pollen parent.

As the result of this breeding, I have produced a new and improved rose variety which is distinguished from its parents, as well as from all other rose varieties of which I am aware, as evidenced by the following unique combination of principal characteristics which are outstanding in the new variety:

1. An extremely vigorous habit of growth which promotes repeat blooming cycles;
2. Constancy of bloom throughout the year;
3. A carnation-like full flower form; and
4. A distinctive and attractive flower color of many shadings, ranging from an almost pure pale yellow color, at times, to a definite "freckled" effect at other times.

In comparison with the seed parent, that variety had unusually large foliage, whereas the foliage of the new variety is of average size; and the flowers of this parent were red and very large in size and formed of large individual petals, whereas the flowers of the new variety have many smaller petals which unfold with a ruffled effect.

As compared with the pollen parent ("Granada"), the flowers of this parent are smaller in size and the flower colors are more definite and distinct and do not change and vary like the yellow blends do in my new variety; the flowers of the new variety have only a slight fragrance while those of this parent are quite fragrant; and my new variety is much more vigorous and considerably more upright in habit than "Granada".

Asexual reproduction of my new variety by budding, as performed by me at Chino, Calif., shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Munsell's Color Cascade, published by Munsell Color Company, Inc., of Baltimore, Md., except where general color terms of ordinary dictionary significance are obvious:

Type: Hardy; fairly tall; bush; outdoor; seedling; for cut flowers and for garden decoration.
Class: Hybrid tea.
Breeding: Seedling.
*Seed parent.*—An unnamed seedling.
*Pollen parent.*—"Granada".
Propagation: Holds its distinguishing characteristics through succeeding propagations by budding.

FLOWERS

Locality where grown and observed: Chino, Calif.
Flowers Borne: From singly to 2 or 3 to stem; in regular clusters; on normally strong, medium long stems.
Quantity of bloom: Free and abundant, both outdoors and in greenhouse.
Continuity: From intermittent to continuous.
Fragrance: Slight.
Bud:
*Peduncle.*—Medium length; mostly medium caliper; erect; smooth; few hairs. Color—Light yellowish green.
*Before calyx breaks.*—Size—From medium to small. Form—From short to medium length; oval but somewhat pointed, with foliaceous appendages on the surface of the bud; with slender bristle-like foliaceous parts extending beyond the tip of the bud equal to from ¼ to ½ or more of its length, Color—Mostly light green.
*As petals first open.*—Size—Small. Form—Short; mostly globular. Color—Outside—Pale Yellow, 27-2. Inside—Pale Yellow, 27-2. Opening—Opens up well.
Bloom:
*Size (when fully open).*—From 2½ inches to 3½ inches.
*Petalage.*—Very double (many petals, but usually with no stamens showing; from 38 to 48 petals; arranged regularly.
*Form.*—Flat, open, full and globular at first, but becoming flat; petals being at first cupped and somewhat rolled inward, but later becoming loosely rolled mostly outward at maturity.

Petals:

*Texture.*—Moderately thick; somewhat leathery; soft.

*Appearance.*—Inside—Velvety. Outside—Somewhat velvety.

*Shape.*—Outside—Obovate; barely scalloped mostly with apex. Intermediate—Obovate; barely scalloped. Inside—Obovate; barely scalloped; with more tapered apex.

This description of a newly opened flower was made from a rose that was grown outdoors in the month of August at Chino, Calif.

*Color.*—Outer petal—Outside surface—Medium pale Yellow, 28-5, blending upward into pinkish Yellow 27-5, with apex border somewhat more Pink, 35-2. Inside surface—Brighter Yellow, 27-6, diffusing ½ way up the petal to light Reddish Pink, 40-5.

*Intermediate petal.*—Outside surface—Medium pale Yellow, 27-5, with minor streaking with hint of very light Pink, 35-1. Inside surface—Medium Yellow, 27-6 at base, blending midway up petal into a salmon pinkish orange, with the Pink being between 39-4 and 40-5.

*Inner petal.*—Outside surface—Bottom half of base being medium Yellow, 27-5, blending upward into pinker Yellow, 28-4, with very, very minor streaking of Pink, 36-1. Inside surface—Medium Yellow, 27-6, at base, blending midway up petal into a salmon pinkish orange, with the Pink being between 39-4 and 40-5, and the very slight Orange shading 29-3.

This description was made from a rose that was open for three days outdoors during the month of August at Chino, Calif.

*Color.*—Outer petal—Outside surface—Bottom third pale Yellow, 26-4, blending upward into streaks of Pink, 36-2, and blending at top to pinkish Orange 33-1. Inside surface—Bottom half pale Yellow 27-3, blending upward into streaks of Pink, 36-2, and further blending at the top to pale Yellow, 27-3.

*Inner petal.*—Outside surface—Pale Yellow, 26-3, with very faint blending ⅔ up into an extremely pale Pink, 36-2, and then blending further to an extremely pale Yellow, 26-2. Inside surface—Bottom half of petal pale Yellowish Orange, 30-5, blending upward into a pale Orange Yellow, between 31-3 and 28-3, with a hint of delicate Pink 36-2, and with tip of apex reverting to pale Yellow 28-2.

*General color effect.*—Newly opened flower—Blend of pale Yellow 27-5 on the outside to streaks of light Pink 39-5 towards the center of the bloom. 3-days open—Generally the same as the newly opened flower, except Pink shading 39-5 almost gone and color has overall effect of a pale Yellowish Orange, 28-2.

*Behavior.*—Drop off cleanly.

*Flower longevity.*—On bush in garden—4 or 5 days in August Cut roses grown outdoors and kept at living room temperatures—3 or 4 days in August.

REPRODUCTIVE ORGANS

Stamens: Medium number; arranged irregularly about pistils; tucked in calyx.

Filaments: Short; most with anthers. Color—Golden yellow.

Anthers: From small to medium size; open at various times. Color—Brown, but mostly with some yellow.

Pollen: Sparse. Color—Lemon yellow.

Pistils: From few to medium number.

Styles: Fairly even; short; loosely separated; columnar.

Stigma: Color—Yellowish red.

Ovaries: All enclosed in calyx.

Hips: None observed.

Sepals: Permanent; medium length; spear-shaped; recurved.

Seeds: None observed.

PLANT

Foliage:

*Leaves.*—Compound of 3–5 leaflets; very abundant; moderately large; moderately heavy.

*Leaflets.*—Shape—Obovate. Apex—Obtuse. Margin—Finely serrate.

*Color.*—Mature—Upper surface—moderately dark green. Under surface—normal yellowish green. Young—Upper surface—moderately green. Under surface—Light green.

*Rachis (the supporting stem of the compound leaf).*—Heavy weight. Upper side—Smooth; grooved; somewhat hairy. Under side—Smooth

*Stipules.*—Long; from medium width to wide; with long points turning out at an angle of 45°.

Disease and insect resistance: No evidence of blackspot, and above average resistance to powdery mildew; and normal good resistance to usual rose insects, as determined by comparison with other rose varieties grown under the same field conditions at Chino, Calif.

Growth:

*Habit.*—Bushy; upright; much-branched.

*Growth.*—Very vigorous.

*Canes.*—Moderately heavy caliper.

*Main Stems.*—Color—Medium green. Large prickles—Several; medium length; slightly hooked downward; with oval base. Color—From grayish to light tan brown. Small prickles—None to few. Hairs—None.

*Branches.*—Color—Dull green. Large prickles—Several; from medium length to long; hooked downward; with long, oval base. Color—Brown. Small prickles—few. Hairs—None.

*New Shoots.*—Color—Medium reddish at the start, turning to light reddish green and then finally to yellowish green. Large prickles—Few; from short to medium length; hooked slightly downward; with oval base. Color—Olive green.

*Small prickles.*—None to few. Color—Reddish brown.

*Hairs.*—Few. Color—Reddish.

I claim:

1. A new and distinct variety of rose plant of the hybrid tea class, substantially as herein shown and described, characterized particularly as to novelty by the unique combination of an extremely vigorous habit of growth which promotes repeat blooming cycles; constancy of bloom throughout the year; a carnation-like full flower form; and a distinctive and attractive flower color of many shadings, ranging from an almost pure pale yellow color, at times, to a definite "freckled" effect at other times.

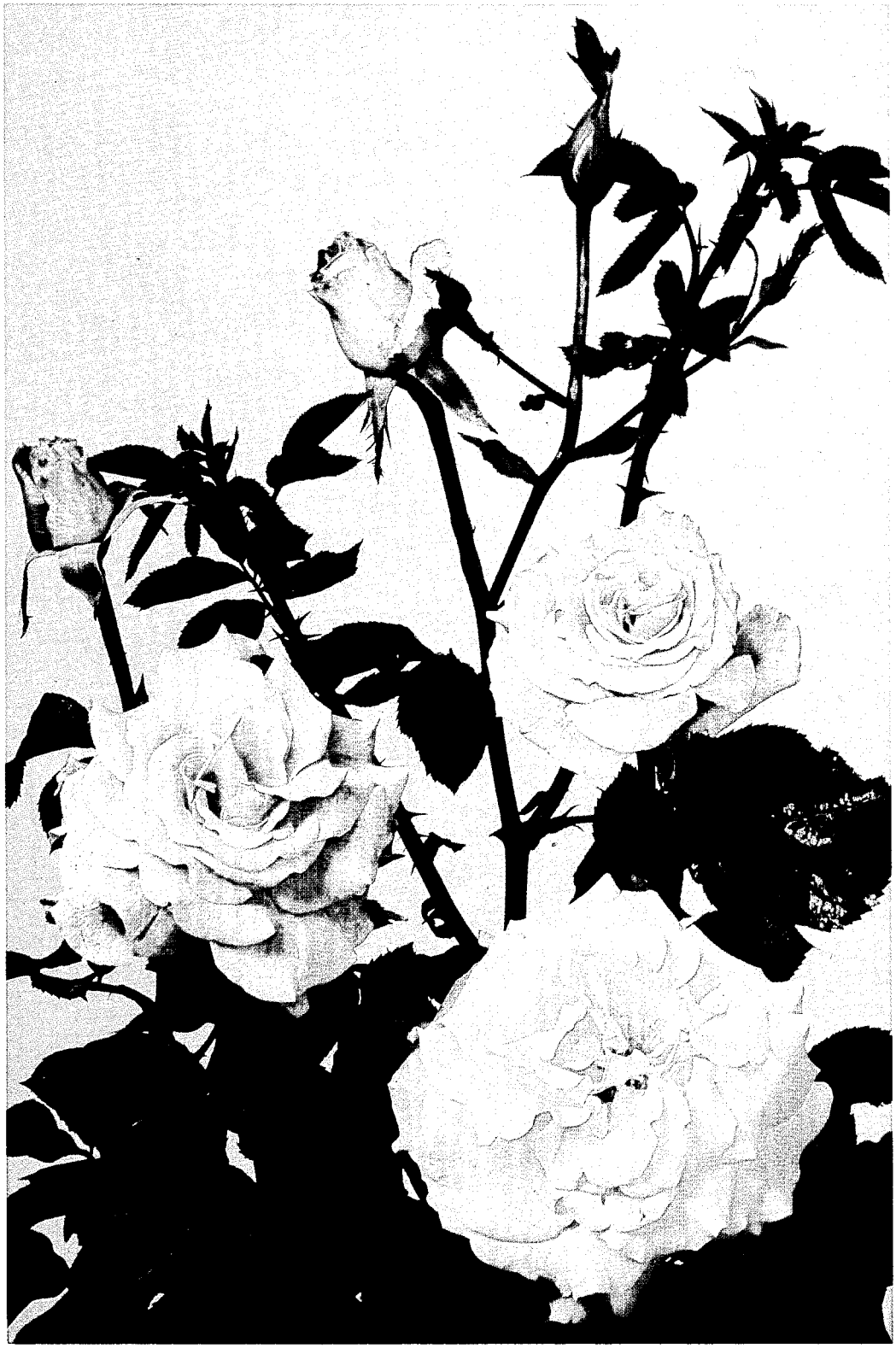

* * * * *